US00PP25520P3

(12) United States Plant Patent
Danziger

(10) Patent No.: US PP25,520 P3
(45) Date of Patent: May 5, 2015

(54) ***ANGELONIA* PLANT NAMED 'DALON11'**

(50) Latin Name: *Angelonia angustifloria*
Varietal Denomination: DALON11

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 13/986,279

(22) Filed: Apr. 18, 2013

(65) Prior Publication Data

US 2014/0317817 P1 Oct. 23, 2014

(51) Int. Cl.
*A01H 5/00* (2006.01)

(52) U.S. Cl.
USPC ..... Plt./404

(58) Field of Classification Search
USPC ..... Plt./404
See application file for complete search history.

(56) References Cited

PUBLICATIONS

UPOV Record Detail for 'DALON11' printed May 19, 2014.*
Danziger Flower Farm, Sep. 26, 2012.*

* cited by examiner

*Primary Examiner* — Susan McCormick Ewoldt
*Assistant Examiner* — Keith Robinson
(74) *Attorney, Agent, or Firm* — Cassandra Bright

(57) ABSTRACT

A new and distinct *Angelonia* cultivar named 'DALON11' is disclosed, characterized by large indigo colored flowers. The new variety is free branching and flowering with upright plant habit and good garden performance. The new variety is an *Angelonia*, normally produced as an outdoor garden or container plant.

2 Drawing Sheets

Figure 1:
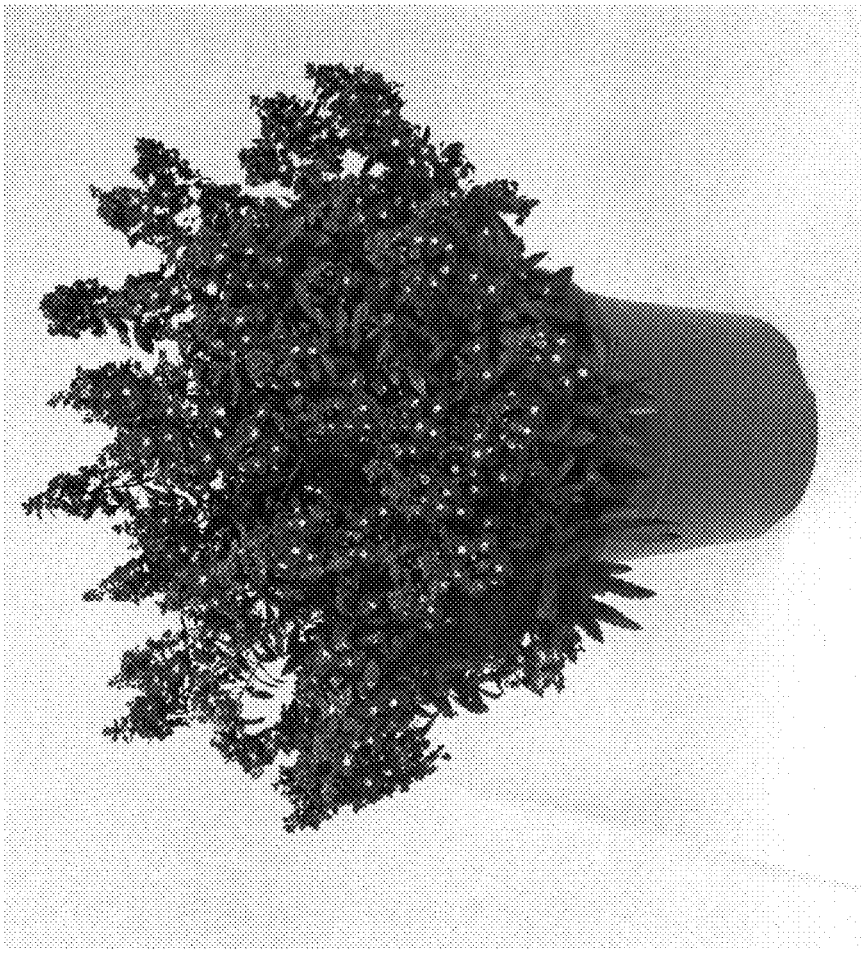

Latin name of the genus and species: *Angelonia angustifloria.*

Variety denomination: 'DALON11'.

BACKGROUND OF THE INVENTION

The new *Angelonia* cultivar is a product of a planned breeding program conducted by the inventor, Gavriel Danziger, in Moshav Mishmar Hashiva, Israel. The objective of the breeding program was to produce new *Angelonia* varieties for ornamental commercial applications. The cross resulting in this new variety was made during April of 2009.

The seed parent is the unpatented, proprietary seedling variety referred to as *Angelonia angustifloria* 'AL-497' The pollen parent is the unpatented, proprietary seedling variety referred to as *Angelonia angustifloria* 'AL-511'. The new variety was discovered in October of 2010 by the inventor in a group of seedlings resulting from the 2009 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in October of 2010 and has shown that the unique features of this cultivar are stable and reproduced true to type in successive generations.

SUMMARY OF THE INVENTION

The cultivar 'DALON11' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DALON11' These characteristics in combination distinguish 'DALON11' as a new and distinct *Angelonia* cultivar:

1. Upright plant habit.
2. Freely branching habit.
3. Freely flowering habit.
4. Large indigo colored flowers.
5. Good garden performance.

Plants of the new cultivar 'DALON11' are similar to plants of the seed parent, *Angelonia angustifloria* 'AL-497' in most horticultural characteristics, however, plants of the new cultivar 'DALON11' produces a plant with a larger flower size than the seed parent. 'DALON11' also has a darker flower color than the seed parent.

Plants of the new cultivar 'DALON11' are similar to plants of the pollen parent; *Angelonia angustifloria* 'AL-511', unpatented, in most horticultural characteristics, however, plants of the new cultivar 'DALON11' produce smaller flowers as well as a less vigorous growth habit than the pollen parent.

COMMERCIAL COMPARISON

Plants of the new cultivar 'DALON11' are comparable to the variety *Angelonia* 'Alonia Dark Blue' unpatented. The two *Angelonia* varieties are similar in most horticultural characteristics; however, the new variety 'DALON11' differs in producing larger and darker flowers as well as more vigorous growth than the comparator.

Plants of the new cultivar 'DALON11' can also be compared to the commercial variety *Angelonia* 'DALON9' U.S. Plant Pat. No. 22,912. These varieties are similar in most horticultural characteristics; however 'DALON11' produces a darker flower color as well as being more branched in growth habit than 'DALON9'.

BRIEF DESCRIPTION OF THE PHOTOGRAPHS

The accompanying photograph in FIG. 1 illustrates in full color a typical plant of 'DALON11' grown in a greenhouse, in a 13 cm pot. Age of the plant photographed is approximately 9 weeks from a rooted cutting.

Figure 2:
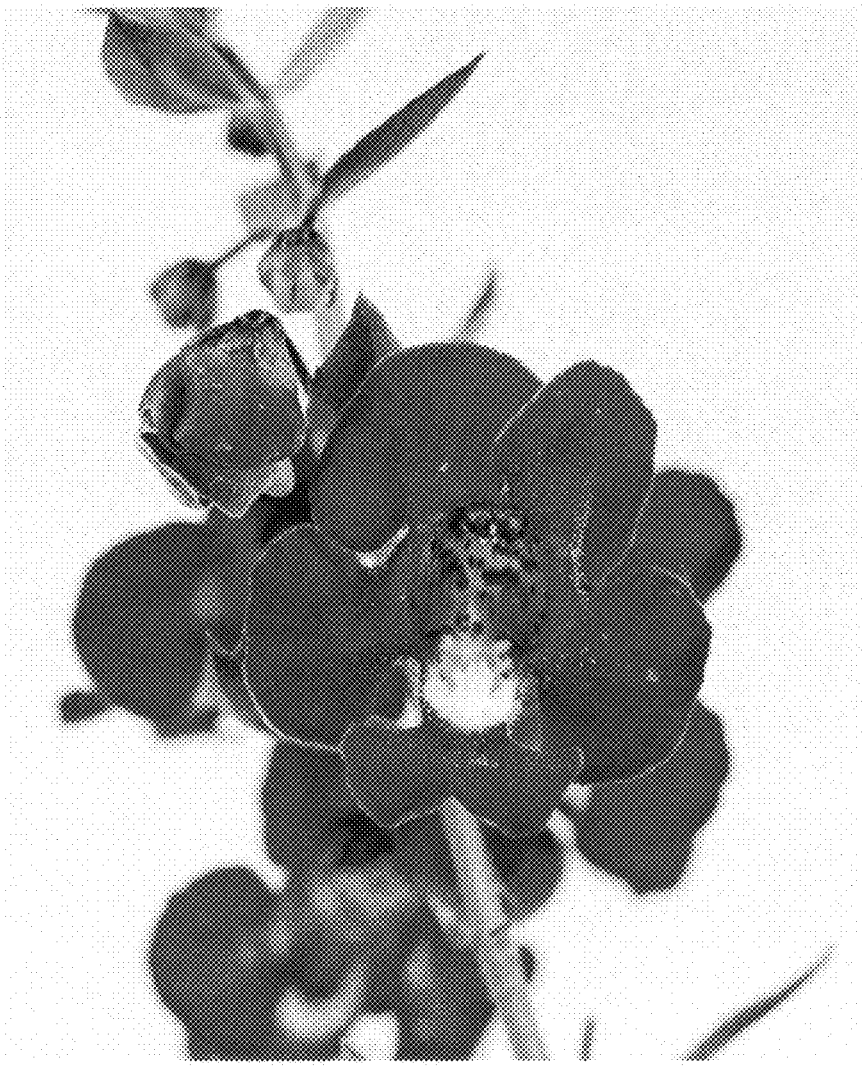

FIG. 2 illustrates in full color a close up of a typical bloom of 'DALON11'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DALON11' plants grown outdoors during, Spring, Summer, and Autumn in Moshav Mishmar Hashiva, Israel. The growing temperature ranged from 20° C. to 30° C. during the day and from 15° C. to 25° C. during the night. General light conditions are bright, normal sunlight. Measurements and numerical values represent averages of typical plant types.

Botanical classification: *Angelonia angustifloria* 'DALON11'.

PROPAGATION

Time to initiate roots: About 10 to 15 days at approximately 22° C.

Root description: Branched.

PLANT

Age of plant described: Approximately 70 days from rooted cutting.

Pot size of plant described: 13 cm.

Growth habit: Erect.

Height:

- *To top of foliage.*—30 cm.
- *To top of flowers.*—30 cm.

Plant spread: 30 cm.

Growth rate: Fast.

Branching characteristics: Medium.

Length of primary lateral branches: 30 cm.

Diameter of lateral branches: 0.5 cm.

Quantity of primary lateral branches: 6-8.

Characteristics of primary lateral branches:

- *Form.*—Round.
- *Diameter.*—0.5 cm.
- *Color.*—Yellow-green group 144D RHS.
- *Texture.*—Smooth.
- *Strength.*—Breakable.

Internode length: 1.5-2 cm.

FOLIAGE

Leaf:

- *Arrangement.*—Opposite.
- *Quantity.*—Approximately 20-25 per branch.
- *Average length.*—2.5-9 cm.
- *Average width.*—1.5 cm.
- *Shape of blade.*—Lanceolate.
- *Apex.*—Rounded.
- *Base.*—Pointed.
- *Margin.*—Scalloped.
- *Texture of top surface.*—Smooth.
- *Appearance.*—Moderately glossy upper surface, matte lower surface.
- *Pubescence.*—No.
- *Aspect.*—50°.
- *Color.*—Young foliage upper side: Green group 137A RHS. Young foliage under side: Green group 137D RHS. Mature foliage upper side: Green group 137A RHS. Mature foliage under side: Green group 137C RHS.
- *Venation.*—Type: Pinnate. Venation color upper side: Green group 137A RHS. Venation color under side: Green group 137C RHS.
- *Petiole.*—No Petiole.

FLOWER

Natural flowering season: Approximately April through September in Israel.

Days to flowering from rooted cutting: 60.

Inflorescence and flower type and habit: Panicle.

Rate of flower opening: 4 to 14 days from bud to fully opened flower.

Flower longevity on plant: 5 days.

Flower longevity on plant: 5 days.

Persistent or self-cleaning: Self-Cleaning.

Bud:

- *Shape.*—Round.
- *Length.*—0.5 cm.
- *Diameter.*—0.5 cm.
- *Color.*—Yellow-green group 145B RHS.

Flower size:

- *Diameter.*—3 cm.
- *Length.*—2.5 cm.

Flower chamber:

- *Diameter.*—2.1 cm.
- *Length.*—1.8 cm.
- *Coloration.*—Sparse to moderately dense speckling. Background coloration near White 155C, speckles near Violet 86A.

Flower pouch coloration: Near Violet 86A.

Nectary bulge coloration: Near Violet 86B.

Petals:

- *Length.*—1 cm.
- *Diameter.*—1.2 cm.
- *Quantity.*—5.
- *Texture.*—Smooth.

Color:

- *When opening.*—Upper surface: Violet group 86A RHS. Lower surface: Violet group 86B RHS.
- *Fully opened.*—Upper surface: Violet group 86A RHS. Lower surface: Violet group 86B RHS.

Sepals:
*Quantity per flower.*—5.
*Shape.*—Ovate.
*Length.*—0.5 cm.
*Width.*—0.3 cm.
*Apex.*—Acute.
*Base.*—Stitched.
*Margin.*—Entire.
*Texture.*—Smooth.
*Color.*—Green group 137C RHS.
Peduncle: No peduncle.
Pedicel:
*Length.*—1-2 cm.
*Diameter.*—0.1 cm.
*Color.*—Purple group 79A RHS.
Fragrance: Delicate.

REPRODUCTIVE ORGANS

Stamens:
*Number.*—4.
*Filament length.*—3 mm.
Anthers:
*Shape.*—Elliptic.
*Length.*—About 2 mm.
*Color.*—Violet group N88A RHS.
Pollen:
*Color.*—White group 155D RHS.
*Quantity.*—Moderate.
Pistil:
*Number.*—1.
*Length.*—0.3 cm.
*Style.*—Length: 0.4 cm. Color: White group 155D RHS.
*Stigma.*—Shape: Thorn. Color: White group 155D RHS.

OTHER CHARACTERISTICS

Seeds and fruits: If present, capsule 0.5 cm long with 50-75 seeds.
Disease/pest resistance: Neither resistance nor susceptibility to the normal diseases and pests of *Angelonia* have been observed. Pests common to *Angelonia* include Aphids and thrips. Typical diseases are *Botrytis* and *Pythium.*
Temperature tolerance: 5-40° C.

What is claimed is:

1. A new and distinct cultivar of *Angelonia* plant named 'DALON11' as herein illustrated and described.

* * * * *